United States Patent [19]
Mitsui et al.

[11] Patent Number: 4,528,409
[45] Date of Patent: Jul. 9, 1985

[54] PROCESS FOR THE PREPARATION OF CYCLIC ALCOHOL

[75] Inventors: Osamu Mitsui; Yohei Fukuoka, both of Kurashiki, Japan

[73] Assignee: Asahi Kasei Kogyo Kabushiki Kaisha, Japan

[21] Appl. No.: 513,030

[22] Filed: Jul. 12, 1983

[30] Foreign Application Priority Data

Apr. 15, 1983 [JP] Japan ................................. 58-66792

[51] Int. Cl.³ .............................................. C07C 29/04
[52] U.S. Cl. ................................... 568/835; 568/832
[58] Field of Search ............... 568/835, 838, 839, 831, 568/832, 833

[56] References Cited

U.S. PATENT DOCUMENTS

| | | | |
|---|---|---|---|
| 2,477,380 | 7/1949 | Kreps | 260/641 |
| 2,579,601 | 12/1951 | Nelson | 260/641 |
| 3,758,615 | 9/1973 | Wadsworth | 260/659 A |
| 3,988,379 | 10/1976 | Platz et al. | 568/835 |

FOREIGN PATENT DOCUMENTS

| | | | |
|---|---|---|---|
| 642149 | 6/1962 | Canada | 568/835 |
| 686257 | 5/1964 | Canada | 568/835 |
| 43-8104 | 3/1968 | Japan | 568/835 |
| 43-16125 | 7/1968 | Japan | 568/835 |
| 26656 | 11/1969 | Japan | 568/835 |
| 51-13711 | 2/1976 | Japan | 568/385 |
| 1281120 | 7/1972 | United Kingdom | 568/835 |

OTHER PUBLICATIONS

Odioso, "Direct Hydration of Olefins", Ind. & Eng. Chem., 53, 209 (1961).
Muller, "Die Hydratation von Äthen und Propen", Brennstoff Chem., 38, 321–329 (1957) and 357–362 (1957).

Primary Examiner—Werren B. Lone
Attorney, Agent, or Firm—Berman, Aisenberg & Platt

[57] ABSTRACT

The catalytic hydration of a cycle olefin in the co-presence of an aromatic sulfonic acid and a heteropoly acid has been found to be extremely effective for preparing a cyclic alcohol efficiently and in high yield.

16 Claims, 1 Drawing Figure

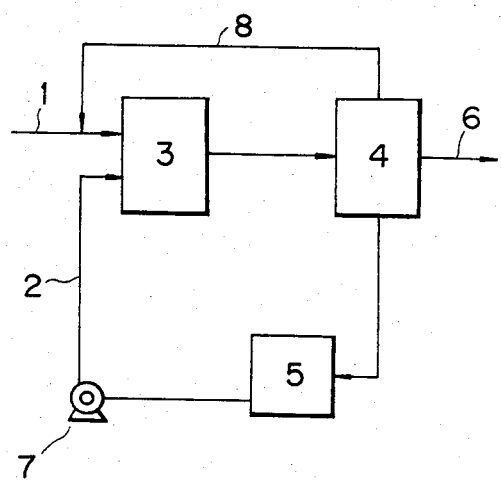
FIGURE

PROCESS FOR THE PREPARATION OF CYCLIC ALCOHOL

The present invention relates to a process for the preparation of a cyclic alcohol. More particularly, the present invention is concerned with a process for the preparation of a cyclic alcohol from a cyclic olefin by a catalytic hydration reaction, in which the catalytic hydration reaction is carried out in the co-presence of an aromatic sulfonic acid and a heteropoly acid, thereby enabling the desired cyclic alcohol to be efficiently produced in high yield.

Cyclic alcohols are generally used as an organic solvent. Besides the use as the organic solvent, cyclic alcohols are also useful as raw materials for the commercial production of various chemical products. For example, cyclohexanol is useful as an intermediate for the preparation of adipic acid and caprolactam. Cyclooctanol and cyclododecanol are useful as raw materials for the preparation of suberic acid and dodecandioic acid, respectively.

Hydration of an olefin is known as a method of producing an alcohol. In this connection, the followings are known: Where an α-olefin, such as ethylene or propylene, is used as a material to be subjected to catalytic hydration to form an alcohol, the hydration reaction proceeds relatively fast. In contrast, where a straight chain internal olefin is subjected to catalytic hydration to form an alcohol, the rate of hydration reaction is extremely low as compared with the case of the α-olefin, and, hence, the kind of a catalyst employable for the reaction is limited. On the other hand, where a cyclic olefin is used as a material to be subjected to catalytic hydration, the rate of hydration reaction is lower than that of the straight chain internal olefin. In addition, the hydration of a cyclic olefin leads to formation of undesirable by-products, such as an isomer of the cyclic olefin. For these reasons, when a cyclic olefin is used as a material to be subjected to catalytic hydration to form an alcohol, the kind of catalyst employable for the reaction is further limited as compared with the case of the straight chain internal olefin.

To produce an alcohol from an olefin by a catalytic hydration reaction, various methods have hitherto been proposed. For example, there has been proposed a method in which an olefin is first subjected to esterification in the presence of highly concentrated sulfuric acid as a catalyst, and the so-formed ester is then subjected to hydrolysis to form an alcohol.

There has also been proposed a method in which an olefin is subjected to hydration reaction in the presence of a catalyst comprising phosphoric acid absorbed in a solid support (see, for example, U.S. Pat. No. 2,579,601) and a method in which an olefin is subjected to hydration reaction in the presence of a cation exchange resin as a catalyst [see, for example, U.S. Pat. No. 2,477,380 and Ind. & Eng. Chem. 53, 209 (1961)].

With respect to the method in which highly concentrated sulfuric acid is used as the catalyst, there are such disadvantages that recovery of the highly concentrated sulfuric acid requires great expense, and due to a strong corrosive action of the highly concentrated sulfuric acid, the apparatus used for the reaction tends to undergo corrosion during the course of the reaction. Because of such disadvantages, the method in which highly concentrated sulfuric acid is used as a catalyst is defective from a practical viewpoint.

In the meantime, it is known to use heteropoly acids, such as a silicotungstic acid, a phosphomolybdic acid, a phosphotungstic acid or the like as a catalyst for the catalytic hydration of a straight chain olefin [see, for example, Brennstoff Chem., 38, 321–329 and 357–362 (1957) and British Patent Specification No. 1,281,120]. However, the heteropoly acid incorporated in the reaction system tends to undergo reduction, forming a precipitate of a metal oxide during the course of the reaction. The formation of such precipitate in the reaction system leads to not only occurrence of serious troubles, for example, scaling or clogging in apparatus, such as a pipe, a valve or a heat exchanger, but also occurrence of side reactions, such as formation of an ether and polymerization of the olefin. In order to eliminate such problems as described above, there was proposed a method in which a straight chain olefin is subjected to catalytic hydration using as a catalyst an aqueous solution containing a heteropoly acid at a relatively low concentration and adjusted to have a pH value of 2.0 to 4.5 by addition of an alkali (see, for example, U.S. Pat. No. 3,758,615). However, such method is also defective since the conversion of the straight chain olefin obtained in a oncethrough operation (one-pass conversion) is extremely small (several percent). As previously stated, where a cyclic olefin is subjected to hydration, the hydration reaction proceeds more slowly than the case of a straight chain olefin. Accordingly, it is well expected that if a cyclic olefin is subjected to hydration by the method disclosed in the above-mentioned U.S. Pat. No. 3,758,615, the conversion of the cyclic olefin will be still smaller than that obtained in the case of the straight chain olefin.

Further, in Japanese Patent Application Laid-Open Specification No. 51-13711, there is disclosed a method in which an olefin is subjected to hydration using as a catalyst an aqueous solution of a heteropoly acid of which the heteropoly acid concentration is in the range of 10 to 70% by weight, and the hydration reaction is effected at a temperature of 100° to 170° C. However, according to the experiment conducted by the present inventors following the teaching disclosed in the above-mentioned Japanese Patent Application Laid-Open Specification No. 51-13711, it has been revealed that the method disclosed in Japanese Patent Application Laid-Open Specification No. 51-13711 is defective; not only is the rate of the hydration reaction low but also the heteropoly acid incorporated in the reaction system also tends to undergo reduction during the course of the reaction, thus causing a precipitate of a metal oxide to be formed in the reaction system, and the formation of such precipitate in the reaction system causes troubles, such as scaling or clogging in apparatus, and causes side reactions, such as formation of an ether and polymerization of the olefin. For the above reasons, the method disclosed in the Japanese Patent Application Laid-Open Specification No. 51-13711 is also defective from a practical viewpoint.

Further, a method of producing a cyclic alcohol by a catalytic hydration reaction in which a cyclic olefin is subjected to a hydration reaction in the presence of an aromatic sulfonic acid as a catalyst is known from Japanese Patent Application Publication Specification Nos. 43-8104 and 43-16125. However, the method of the kind as mentioned above has such a disadvantage that, under the reaction conditions employed in the above method, the aromatic sulfonic acid used as the catalyst exerts a strong corrosive action, and hence, it is required to use glass lining in order to protect the apparatus employed for the production from undergoing corrosion. However, glass lining generally requires a great expense, and, further, the glass inherently is subject to breakage and, therefore, the glass-lined apparatus is extremely difficult in handling. Because of such disadvantage, the method disclosed in Japanese Patent Publication Specification Nos. 43-8104 and 43-16125 in which a cyclic olefin is subjected to hydration reaction in the presence of an aromatic sulfonic acid as a catalyst is defective from a practical viewpoint.

The present inventors have made extensive and intensive studies with a view to eliminating the drawbacks of the conventional methods and to providing a process for preparing a cyclic alcohol from a cyclic olefin by catalytic hydration reaction efficiently and in high yield. As a result, the present inventors have found that, in the production of a cyclic alcohol from a cyclic olefin by a catalytic hydration reaction, the desired cyclic alcohol can be efficiently produced in high yield, without a fear of corrosion of the reaction apparatus, by effecting the catalytic hydration reaction in the co-presence of an aromatic sulfonic acid and a heteropoly acid. The present invention has been made based upon such a novel finding.

Therefore, it is an object of the present invention to provide a process for producing a cyclic alcohol in which a cyclic alcohol is produced from a cyclic olefin by catalytic hydration reaction efficiently and in high yield.

The foregoing and other objects, features and advantages of the present invention will be apparent to those skilled in the art from the following detailed description and appended claims taken in connection with the accompanying drawing in which:

The FIGURE is a flow diagram illustrating one mode of the process of the present invention in which the desired cyclic alcohol is produced in a continuous manner.

According to the present invention, there is provided a process for the preparation of a cyclic alcohol from a cyclic olefin, which comprises subjecting a cyclic olefin to a catalytic hydration reaction using a reaction system including the cyclic olefin and an aqueous solution comprising water and an aromatic sulfonic acid as a catalyst, and wherein said aqueous solution further comprises a heteropoly acid.

The present invention will now be described in detail.

According to the present invention, the kind of a cyclic olefin to be used as a starting material for the production of a cyclic alcohol is not critical. But, in general, there may advantageously be employed a cyclic olefin represented by the general formula (I)

$$C_nH_{2n-2-m}R_m \qquad (I)$$

wherein R represents a hydrogen atom, an alkyl group having 1 to 4 carbon atoms, a phenyl group or a cyclohexyl group, n is an integer of 5 to 12, and m is an integer of 1 to 4.

As the cyclic olefin represented by the above formula (I), there can be mentioned cyclopentene, cyclohexene, cyclooctene, cyclononene, cyclodecene, cycloundecene, cyclododecene, methylcyclohexene, dimethylcyclohexene, trimethylcyclohexene, tetramethylcyclohexene, phenylcyclohexene, and the like. These cyclic olefins may be employed alone or in combination. Further, it should be noted that in the process of the invention, as the starting material, there may be employed a mixture of a cyclic olefin and hydrocarbons other than the cyclic olefin. Generally, in the production of a cyclic olefin, it is difficult to obtain a cyclic olefin in pure form. For example, cyclohexene is produced by subjecting cyclohexane halide to dehalogenation or subjecting cyclohexane to dehydrogenation. In the former method, it is difficult to suppress the formation of by-products, such as benzene, cyclohexane or the like, due to occurrence of a disproportionation reaction. On the other hand, in the latter method, it is difficult to attain a 100% conversion of cyclohexane and to attain a 100% selectivity for cyclohexene. Accordingly, in the commonly employed production process, cyclohexene tends to be obtained in the form of a mixture of cyclohexene and other hydrocarbons, such as cyclohexane or benzene. Methylcyclohexene, which is generally produced by partial hydrogenation of toluene, also tends to be obtained in the form of a mixture of methylcyclohexene, toluene and methylcyclohexane. In the preparation of cyclooctene in which cyclooctadiene is subjected to partial hydrogenation, cyclooctene is obtained in the form of a mixture of cyclooctene and cyclooctane. In the meantime, for example, when cyclohexene containing benzene is subjected to a catalytic hydration reaction by the conventionally employed method in which highly concentrated sulfuric acid is employed as a catalyst, the benzene is reacted with the sulfuric acid, thereby causing a great amount of undesirable by-products to be formed. In contrast, according to the process of the present invention, even if a cyclic olefin containing hydrocarbons other than the cyclic olefin is subjected to hydration reaction, the desired cyclic alcohol can, surprisingly and unexpectedly, be obtained easily without the above-mentioned problem of formation of undesirable by-products.

Accordingly, in the process of the present invention, as the starting material, there may be employed a cyclic olefin containing at least one member selected from the group consisting of an aromatic hydrocarbon and a cyclic paraffin in an amount of about 80 mole % or less, preferably 50 mole % or less based upon the total amount of the cyclic olefin. As examples of the aromatic hydrocarbon which may be contained in the cyclic olefin, there can be mentioned benzene, toluene, xylene, diphenyl, and the like. As examples of the cyclic paraffin which may be contained in the cyclic olefin, there can be mentioned cyclohexane, cyclooctane, and the like.

In the process of the present invention, the cyclic olefin is subjected to a catalytic hydration reaction using a reaction system including the cyclic olefin and an aqueous solution comprising water, an aromatic sulfonic acid and a heteropoly acid.

As the aromatic sulfonic acid to be used as a catalyst in the process of the present invention, there can be mentioned benzenesulfonic acid, naphthalenesulfonic acid, anthracene-sulfonic acid and ($C_1$-$C_3$)alkyl mono- or di-substituted derivatives thereof. Among them, the alkylbenzenesulfonic acid is preferred. An especially preferred alkylbenzenesulfonic acid is p-toluenesulfonic acid.

As the heteropoly acid to be used in combination with the aromatic sulfonic acid in the process of the present invention, there can be mentioned heteropoly acids, each of which contain, as poly atom, at least one member selected from the group consisting of Mo, W and V and each contains, as central atom, at least one member selected from the group consisting of P, As, Si, Ge, Ti, Ce, Th, Mn, Ni, Te, I, Co, Cr, Fe, Ga, B, V, Pt, Be and Zn, and in each of which acids the poly atom and central atom are present at an atomic ratio of 2.5 to 12. The heteropoly acids may be employed not only in the form of a monomer but also in the form of a polymer, such as a dimer or a trimer.

As illustrative examples of the heteropoly acid to be employed in the process of present invention, there can be mentioned a phosphomolybdic acid, a phosphotungstic acid, a phosphomolybdotungstic acid, a phosphomolybdovanadic acid, a phosphomolybdotungstovanadic acid, a phosphotungstovanadic acid, a phosphomolybdoniobic acid, a phosphomanganesetungstic acid, a silicomolybdic acid, a silicotungstic acid, a silicomolybdotungstic acid, a silicomolybdotungstovanadic acid, a boromolybdic acid, a borotungstic acid, a boromolybdotungstic acid, a boromolybdovanadic acid, a boromolybdotungstovanadic acid, a cobaltmolybdic acid, a cobalttungstic acid, and the like. They may be employed alone or in mixture. Among them, a phosphomolybdic acid, a phosphotungstic acid, a silicotungstic acid and a borotungstic acid are preferred. The above-mentioned heteropoly acids may be incorporated in the form of a salt, such as an ammonium salt or an alkali metal salt.

By the use of the heteropoly acid in combination with the aromatic sulfonic acid, according to the process of the present invention, the corrosive action of the aromatic sulfonic acid is surprisingly and unexpectedly suppressed. Further, by the combined use of the heteropoly acid and the aromatic sulfonic acid, a remarkable improvement can be attained as to the conversion of the cyclic olefin.

In the process of the present invention, the total amount of the aromatic sulfonic acid and the heteropoly acid is 5 to 80% by weight, preferably 20 to 70% by weight based upon the amount of the aqueous solution. When the total amount of the aromatic sulfonic acid and the heteropoly acid is smaller than 5% by weight based upon the amount of the aqueous solution, the rate of hydration reaction is unfavorably low.

On the other hand, in the process of the present invention, the total amount of the aromatic sulfonic acid and the heteropoly acid may be 0.1 to 200 parts by weight, preferably 1 to 50 parts by weight per part by weight of the cyclic olefin. If the total amount of the aromatic sulfonic acid and the heteropoly acid is smaller than 0.1 part by weight per part by weight of the cyclic olefin, the rate of hydration reaction is unfavorably low. On the other hand, the use of too large a total amount of the aromatic sulfonic acid and the heteropoly acid is undesirable from an economical viewpoint.

In the process of the present invention, the amount of water to be used is not critical, but generally water is employed in an amount of from 0.5 to 1000, preferably 1 to 500, in terms of molar ratio of the water to the cyclic olefin. Too small an amount of water is unfavorable from a viewpoint of viscosity of the reaction system. On the other hand, in case the amount of water is too large relative to the amount of the cyclic olefin, if the total amount of the aromatic sulfonic acid and the heteropoly acid is comparatively small with respect to the cyclic olefin, the rate of the hydration reaction is unfavorably low. In such case, the rate of the hydration reaction can be increased by increasing the total amount of the aromatic sulfonic acid and the heteropoly acid, but the employment of an increased total amount of the aromatic sulfonic acid and the heteropoly acid leads to an economical disadvantage.

With respect to the amount of the heteropoly acid, the heteropoly acid may be employed in an amount sufficient to attain a corrosion preventing effect. The term "corrosion preventing effect" as used herein is intended to mean such an effect that the materials commonly used for the apparatus in the chemical industry (e.g. stainless steel) have such a reduced corrosion rate as 0.5 mm/year or less. The method of calculation of such corrosion rate will be mentioned later with reference to Examples. The above-mentioned amount varies depending upon the kind of the heteropoly acid, the reaction temperature or the like. For example, in the case of a phosphomolybdic acid, when the hydration reaction is carried our at a temprature of 100° to 120° C., the phosphomolybdic acid can attain a corrosion preventing effect even used in such a small amount as 10 ppm based upon the amount of the aqueous solution. On the other hand, with respect to a phosphotungstic acid and a silicotungstic acid, when the hydration reaction is carried out at a temperature of 120° C. or so, they cannot attain a corrosion preventing effect unless used in an amount of 1% by weight or more based upon the amount of the aqueous solution. Generally, the heteropoly acid may be employed in an amount of 0.001 to 70% by weight based upon the amount of the aqueous solution. When the use of heteropoly acid is intended only for the corrosion prevention, the heteropoly acid may preferably be employed in an amount of 0.01 to 40% by weight, more preferably 0.01 to 20% by weight based upon the amount of the aqueous solution. On the other hand, for a simultaneous attainment of an improvement in conversion of the cyclic olefin and the corrosion preventing effect, the heteropoly acid may preferably be employed in an amount of 10 to 60% by weight based upon the amount of the aqueous solution.

According to the process of the present invention, the solubility of the heteropoly acid in the aqueous solution is increased, and, hence, the heteropoly acid can be stably present in the aqueous solution. Accordingly, the undesirable formation of a precipitate of a metal oxide due to the reduction of the heteropoly acid can be sufficiently eliminated. If necessary, the stability of the heteropoly acid in the aqueous solution can be further improved by addition of an inorganic acid, such as phosphoric acid, silicic acid, boric acid, sulfuric acid or the like in the aqueous solution in an amount of 5% by weight or less based on the amount of the heteropoly acid. In this connection, the addition of a halide, such as hydrochloric acid or oxalic acid, is undesirable because such halide may possibly cause corrosion of the apparatus at a certain temperature.

In the present invention, the catalytic hydration reaction is effected at a temperature of 50° to 200° C., preferably 70° to 150° C. When the reaction temperature is lower than 50° C., the rate of hydration reaction is extremely low. On the other hand, when the reaction temperature is higher than 200° C., the selectivity for the desired cyclic alcohol is decreased due to the occurrence of side reactions, such as formation of an ether.

With respect to the pressure at which the catalytic hydration reaction is effected, it is preferred to employ a pressure sufficient to keep the cyclic olefin in the liquid state at the reaction temperature employed. For example, in the case of cyclohexene, if the hydration reaction is effected at a temperature of 100° C., cyclohexene can maintain the liquid state at a pressure of 3

Kg/cm² G or more, and if the hydration reaction is effected at a temperature of 150° C., cyclohexene can maintain the liquid state at a pressure of 10 Kg/cm² G or more. An inert gas, such as nitrogen gas, may be introduced in the reaction system in order to obtain the necessary reaction pressure.

In the process of the present invention, the reaction time may be varied depending upon the concentration of the catalyst in the aqueous solution, the weight ratio of the catalyst to the cyclic olefin and the reaction temperature. But, in general, when the catalytic hydration reaction is carried out in a batch-wise manner, a reaction time ranging from several minutes to 100 hours may be employed. On the other hand, when the catalytic hydration reaction is carried out in a continuous manner, a reaction time ranging from several minutes to 10 hours may be employed.

One mode of the process of the present invention will be described with reference to the accompanying drawing. The FIGURE illustrates one mode of the process of the present invention in which the desired cyclic alcohol is produced in a continuous manner.

A cyclic olefin, as the starting material, is introduced into a reactor 3 through a line 1. An aqueous solution of an aromatic sulfonic acid which contains a heteropoly acid is introduced into the reactor 3 through a line 2. As the reactor employable in the process of the present invention, there can be mentioned a reaction vessel equipped with a stirrer, a packed column-type reactor, an external circulationtype reactor and the like. In the reactor 3, the cyclic olefin is subjected to hydration reaction in the co-presence of the aromatic sulfonic acid and the heteropoly acid to form a cyclic alcohol. The outflow solution from the reactor 3 is then introduced into a separator 4, where the outflow solution is separated into the formed cyclic alcohol, an unreacted cyclic olefin and the aqueous solution containing the aromatic sulfonic acid and the heteropoly acid. The formed cyclic alcohol is withdrawn from the separator 4 through a line 6. The unreacted cyclic olefin is recycled to the line 1 through a line 8, and combined with a fresh cyclic olefin and fed to the reactor 3. The aqueous solution of the aromatic sulfonic acid and heteropoly acid withdrawn from the separator 4 is fed to a tank 5 and then recycled into the reactor 3 by means of a pump 7. In this mode, the above-mentioned operation is continued for a predetermined time.

The advantages of the process of the present invention are summarized below.

(1) By the use of a heteropoly acid in combination with an aromatic sulfonic acid, the corrosive action of the aromatic sulfonic acid can be greatly suppressed, and, hence, the apparatus employed for the reaction can be sufficiently prevented from corrosion.

(2) Due to the presence of an aromatic sulfonic acid, as previously stated, the heteropoly acid can be stably present in the aqueous solution. Accordingly, the undesirable formation of a precipitate of a metal oxide due to the reduction of the heteropoly acid can be sufficiently eliminated.

(3) The combined use of an aromatic sulfonic acid and a heteropoly acid brings about synergistically a remarkable improvement in conversion of the cyclic olefin. The conversion of the cyclic olefin attained by the catalytic hydration reaction conducted in the co-presence of an aromatic sulfonic acid and a heteropoly acid is higher than that attained by the catalytic hydration reaction conducted in the presence of an aromatic sulfonic acid alone or a heteropoly acid alone.

The present invention will be illustrated in more detail with reference to the following Examples, which should not be construed to be limiting the scope of the present invention.

In the following Examples and Comperative Examples, the determination of corrosion rate, the evaluation of corrosion resistance, the determination of conversion of the cyclic olefin and the determination of selectivity for the cyclic alcohol were conducted as follows.

A. Determination of corrosion rate

For the determination of the corrosion rate, a piece of each of SUS-304 SUS-316 and SUS-444 [stainless steels in accordance with JIS (Japanese Industrial Standards) G4304-1977] and Ti were employed as a test piece.

A test piece which had been weighed in advance was immersed in the reaction liquid. After completion of the reaction, the test piece was taken out and weighed again. The corrosion rate was calculated by the following equation:

$$\frac{(W/d) \times 8760}{A} \times 10 \text{ (mm/year)}$$

[wherein W is a decrease in weight of the test piece per hour during the reaction (g/hour), which is calculated by the equation:

$$\frac{W_1 - W_2}{t}$$

wherein $W_1$ is a weight (g) of the test piece measured before immersing in the reaction mixture, $W_2$ is a weight (g) of the test piece measured after completion of the reaction, and t is a reaction time (hr), d is a density (g/cm³) of the test piece, and A is a surface area (cm²) of the test piece].

B. Evaluation of corrosion resistance

The corrosion resistance of the test piece was evaluated according to the following criterion:
o: Corrosion rate<0.05 (mm/year)
Δ: 0.05≦Corrosion rate<0.5 (mm/year)
x: 0.5≦Corrosion rate (mm/year).

C. Conversion of cyclic olefin and selectivity for cyclic alcohol

Conversion of cyclic olefin and selectivity for cyclic alcohol are defined as follows.

Conversion of cyclic olefin (%) = (1)

$$\frac{\text{mole number of consumed cyclic olefin}}{\text{mole number of charged cyclic olefin}} \times 100$$

Selectivity for cyclic alcohol (%) = (2)

$$\frac{\text{mole number of formed cyclic alcohol}}{\text{mole number of consumed cyclic olefin}} \times 100$$

EXAMPLE 1

According to the flow-chart illustrated in FIGURE, cyclohexanol was produced from cyclohexene by catalytic hydration reaction.

Illustratively stated, into a reactor 3 which comprises an autoclave made of pressure-resistant glass and equipped with a stirrer, and has an inner diameter of 100 mm and a height of 180 mm were introduced cyclohexene through a feed pipe 1 at a feed rate of 80 g/hr and an aqueous 60% solution of p-toluenesulfonic acid (the weight of p-toluenesulfonic acid excludes the weight of water of crystallization of p-toluenesulfonic acid) containing 2% by weight of a phosphomolybdic acid (the weight of phosphomolybdic acid excludes the weight of water of cystallization of phosphomolybdic acid) (hereinafter often referred to as "catalyst solution") through a feed pipe 2 at a feed rate of 400 g/hr. A piece of stainless steel SUS-304 and a piece of stainless steel SUS-316 were each fixed to one end of separate Tefron-made shafts. The other end of each shaft was fixed to the lid of the autoclave so that the pieces of stainless steel were immersed in the liquid in the autoclave.

The liquid was then stirred at 600 rpm by means of a stirrer, and a catalytic hydration reaction was allowed to proceed at 120° C. under a pressure of 5 Kg/cm² G in an atmosphere of nitrogen gas. An outflow solution from the reactor contained cyclohexanol at a concentration of 10.5% by weight. The outflow solution was then introduced into a separator 4 and separated into the catalyst solution, an unreacted cyclohexene and the formed cyclohexanol. The formed cyclohexanol was withdrawn from the separator through an outlet pipe 6. The unreacted cyclohexene was recycled to the feed pipe 1 through a feed pipe 8, and combined with fresh cyclohexene and fed to the reactor 3 through the feed pipe 1 at a feed rate of 80 g/hr. On the other hand, the catalyst solution was introduced into a catalyst tank 5 and recycled into the reactor 3 through the feed pipe 2. The above operation was continued for 300 hours. During this period, the composition of the outflow solution withdrawn from the reactor 3 was not changed.

Subsequently, the reactor was dismounted and the shaft was taken out of the autoclave. The piece of the stainless steel was detached from the shaft to determine any change in weight. From the results obtained, the corrosion rate of each piece of stainless steel was calculated. The corrosion rate of the SUS-304 was found to be 0.028 mm/year and that of the SUS-316 was found to be 0.011 mm/year.

From the above results, it is apparent that the use of the aqueous solution of p-toluenesulfonic acid containing a phosphomolybdic acid causes substantially no problem as to the corrosion of the apparatus.

COMPARATIVE EXAMPLE 1

In substantially the same manner as described in Example 1, the catalytic hydration reaction was conducted except that the phosphomolybdic acid was not incorporated in the catalyst solution. The corrosion rates of the pieces of the stainless steel SUS-304 and the stainless steel SUS-316 were examined in the same manner as described in Example 1 except that the shaft was taken out from the autoclave after 24 hours from the immersion of the piece in the liquid. The corrosion rates of the stainless steel SUS-304 and the stainless steel SUS-316 were observed to be 36.4 mm/year and 23.8 mm/year, respectively. It was found that the entire surface of each piece of the stainless steel underwent corrosion. In this Example, the concentration of cyclohexanol in the outflow solution withdrawn from the reactor was 6.5% by weight.

EXAMPLES 2 to 6 and COMPARATIVE EXAMPLES 2 and 3

Into a 50 ml-capacity glass-made ampule were charged a phosphomolybdic acid (P:Mo=1:12 in atomic ratio) and p-toluenesulfonic acid in a varied amount ratio so that the total weight of the phosphomolybdic acid and the p-toluenesulfonic acid excluding the weight of water of crystallization of each of the p-toluenesulfonic acid and the phosphomolybdic acid, became 12 g. Then, to the thus obtained mixture was added water in such an amount that the total weight of the water, including the weight of water of crystallization of each of the p-toluenesulfonic acid and the phosphomolybdic acid, became 12 g, and then 1 ml of cyclohexene was further added, thereby to obtain a liquid.

Subsequently, the ampule was sealed and subjected to shaking at a rate of 80 reciprocations per minute at 100° C. for 1 hour. Then, the ampule was opened and the liquid was taken out. To the liquid was added a 3-fold volume of water, followed by extraction with chloroform. The thus obtained chloroform fraction was subjected to gas chromatography, thereby to determine the amounts of unreacted cyclohexene, cylohexanol and by-products in the chloroform. The results obtained are shown in Table 1. On the other hand, into a 500 ml-capacity autoclave, a phosphomolybdic acid (P:Mo=1:12 in atomic ratio), p-toluenesulfonic acid, water and cyclohexene were charged in the same manner as described above. Pieces of various kinds of stainless steel (as indicated in Table 1) and a piece of Ti were each fixed to one end of separate Tefron-made shafts. The other end of each shaft was fixed to the lid of the autoclave so that the respective pieces of stainless steel and that of Ti were immersed in the liquid in the autoclave. The liquid in the autoclave was then stirred at 600 rpm by means of a stirrer at 100° C. for 24 hours. Thereafter, each shaft was taken out from the autoclave, and the pieces were detached from their respective shafts to determine any changes in weight. From the results obtained, the corrosion rate of each piece was calculated; and from the results obtained as to the corrosion rate, the corrosion resistance of each piece was evaluated. The results obtained are shown in Table 1.

As is apparent from the results shown in Table 1, the phosphomolybdic acid incorporated in the reaction system greatly contributed to the prevention of the corrosion. Further, it is apparent that the conversion of cyclohexene obtained in the hydration reaction effected in the copresence of p-toluenesulfonic acid and the phosphomolybdic acid is much higher than that obtained in the hydration reaction effected in the presence of p-toluenesulfonic acid alone or the phosphomolybdic acid alone.

TABLE 1

| Example No. | p-Toluene-sulfonic Acid (g) | Phospho-molybdic Acid (g) | Conversion of Cyclo-hexene (%) | Selectivity for Cyclohexanol (%) | Evaluation of Corrosion Resistance | | | |
|---|---|---|---|---|---|---|---|---|
| | | | | | SUS-444 | SUS-304 | SUS-316 | Ti |
| Comparative Example 2 | 12 | 0 | 30.2 | 96.4 | x | x | x | x |
| Example | 12 | 0.01 | 30.3 | 96.3 | o | o | o | o |

TABLE 1-continued

| Example No. | p-Toluene-sulfonic Acid (g) | Phospho-molybdic Acid (g) | Conversion of Cyclo-hexene (%) | Selectivity for Cyclohexanol (%) | Evaluation of Corrosion Resistance | | | |
|---|---|---|---|---|---|---|---|---|
| | | | | | SUS-444 | SUS-304 | SUS-316 | Ti |
| Example 2 | | | | | | | | |
| Example 3 | 10.8 | 1.2 | 59.3 | 99.8 | o | o | o | o |
| Example 4 | 6.0 | 6.0 | 63.5 | 99.8 | o | o | o | o |
| Example 5 | 3.8 | 8.2 | 62.4 | 99.9 | o | o | o | o |
| Example 6 | 1.2 | 10.8 | 65.3 | 99.8 | o | o | o | o |
| Comparative Example 3 | 0 | 12 | 24.5 | 98.2 | o | o | o | o |

Note:
In Comparative Example 3, precipitates were formed in the reaction mixture

EXAMPLE 7

Into a 500 ml-capacity glass-made autoclave were charged 100 ml of water, 150 g of benzenesulfonic acid, 30 g of a phosphotungstic acid, and 100 ml of cyclohexene containing 40% by weight of benzene and 10% by weight of cyclohexane.

On the other hand, a piece of stainless steel SUS-304 was fixed to one end of a Teflon-made shaft. The other end of the shaft was fixed to the lid of the autoclave so that the piece of stainless steel was immersed in liquid in the autoclave. Then, the liquid was heated to 90° C. with stirring at 800 rpm by means of a stirrer, and held at 90° C. for 3 hours. Thereafter, the shaft was taken out of the autoclave, and the piece of stainless steel was detached from the shaft to determine any change in weight. From the result, the corrosion rate of the piece of SUS-304 was calculated. It was found that the corrosion rate of the SUS-304 was as low as 0.007 mm/year. The liquid was then cooled in water and taken out of the autoclave. Subsequently, to the liquid was added 200 ml of water, followed by extraction with chloroform. The thus obtained chloroform fraction was subjected to gas chromatography, thereby to determine the unreacted cyclohexene, the formed cyclohexanol and by-products in the chloroform.

As a result, it was found that the conversion of cyclohexene was 80%. As the by-product, only a small amount of ether was detected.

EXAMPLES 8 to 19

Cyclohexanol was produced from cyclohexene in substantially the same manner as in Example 7 except that the kind of catalyst, the reaction temperature and the reaction time were varied as indicated in Table 2.

In each of Examples 8 to 19, the corrosion rates of the SUS-304 and the SUS-316 were examined in the same manner as described in Example 7. From the results obtained as to the corrosion rate, the corrosion resistance of each of the SUS-304 and the SUS-316 were evaluated. The conversion of cyclohexene and the selectivity for cyclohexanol were also determined.

The results obtained are shown in Table 2.

TABLE 2

| Example No. | Aromatic Sulfonic Acid | (g) | Heteropoly Acid | (g) | Water (g) | Starting Material Composition | (g) | Temperature (°C.) | Time (hr) | Conversion of Cyclohexene (%) | Selectivity for Cylcohexanol (%) | Evaluation of Corrosion Resistance | |
|---|---|---|---|---|---|---|---|---|---|---|---|---|---|
| | | | | | | | | | | | | SUS-304 | SUS-316 |
| 8 | p-Toluene-sulfonic Acid | 150 | Phospho-molybdic Acid | 1.5 | 80 | Cyclohexene | 15 | 70 | 2 | 85.8 | 100.0 | o | o |
| 9 | p-Toluene-sulfonic Acid | 150 | Phospho-molybdic Acid | 1.5 | 130 | " | 50 | 150 | 0.5 | 78.4 | 97.4 | Δ | o |
| 10 | p-Toluene-sulfonic Acid | 150 | Phospho-molybdic Acid | 0.005 | 100 | " | 25 | 100 | 1 | 80.0 | 99.5 | o | o |
| 11 | p-Toluene-sulfonic Acid | 150 | Phospho-molybdic Acid | 5 | " | Cyclohexene Benzene Cyclohexane | 10 7 3 | 100 | 1 | 86.3 | 99.2 | o | o |
| 12 | p-Toluene-sulfonic Acid | 65 | Phospho-molybdic Acid | 65 | 130 | Cyclohexene Benzene | 5 20 | 100 | 1 | 68.3 | 97.4 | o | o |
| 13 | p-Toluene-sulfonic Acid | 120 | Phospho-molybdic Acid | 0.2 | 120 | Cyclohexene Cyclohexane | 10 5 | 50 | 3 | 38.6 | 100.0 | o | o |
| 14 | Naphthalene-sulfonic Acid | 110 | Silicotungstic Acid | 10 | 100 | Cyclohexene | 30 | 100 | 1 | 68.5 | 99.5 | o | o |
| 15 | p-Toluene-sulfonic Acid | 110 | Silicomolybdic Acid | 10 | 100 | " | 30 | 120 | 1 | 93.1 | 98.3 | o | o |
| 16 | Anthracene-sulfonic Acid | 110 | Phospho-tungsto-Vanadic Acid | 10 | 100 | " | 30 | 120 | 1 | 65.4 | 98.6 | o | o |
| 17 | Benzene- | 110 | Boromolybdo- | 10 | 100 | " | 30 | 80 | 2 | 63.8 | 98.8 | o | o |

TABLE 2-continued

| Example No. | Aromatic Sulfonic Acid | (g) | Heteropoly Acid | (g) | Water (g) | Starting Material Composition | (g) | Temperature (°C.) | Time (hr) | Conversion of Cyclohexene (%) | Selectivity for Cylcohexanol (%) | Evaluation of Corrosion Resistance SUS-304 | SUS-316 |
|---|---|---|---|---|---|---|---|---|---|---|---|---|---|
| | sulfonic Acid | | tungstic Acid | | | | | | | | | | |
| 18 | p-Toluenesulfonic Acid | 110 | Boromolybdic Acid | 10 | 100 | " | 30 | 110 | 0.75 | 76.4 | 99.8 | o | o |
| 19 | p-Toluenesulfonic Acid | 110 | Borotungstic Acid | 10 | 100 | " | 30 | 60 | 2 | 33.8 | 100.0 | o | o |

EXAMPLES 20 to 26

Various cyclic alcohols were produced in substantially the same manner as described in Example 7 except that the kind of cyclic olefin, the kind of catalyst, the reaction temperature and the reaction time were varied as indicated in Table 3. The results obtained are shown in Table 3. On the other hand, in each of Examples 20 to 26, the corrosion rate of the SUS-316 was examined in the same manner as described in Example 7. In each of Examples 20 to 26, the corrosion rate of the SUS-316 was found to be 0.05 mm/year or less.

TABLE 3

| Example No. | Starting Material Composition | (g) | Aromatic Sulfonic Acid | (g) | Heteropoly Acid | (g) | Water (g) | Temperature (°C.) | Time (hr) | Conversion of Cyclic olefin (%) | Selectivity for Cyclic alcohol (%) |
|---|---|---|---|---|---|---|---|---|---|---|---|
| 20 | 1-Methylcyclohexene | 25 | p-Toluenesulfonic Acid | 100 | Silicotungstic Acid | 20 | 100 | 80 | 1.5 | 85.3 | 95.4 |
| 21 | 1,3-Dimethylcyclohexene m-Xylene | 10 15 | Benzenesulfonic Acid | 150 | Phosphomolybdic Acid Phosphomolybdic Acid | 5 5 | " | 90 | 1.0 | 80.2 | 78.2 |
| 22 | 1,3,6-Trimethylcyclohexene | 50 | p-Toluenesulfonic Acid | 145 | Phosphomolybdic Acid | 5 | " | 120 | 2.0 | 58.4 | 93.2 |
| 23 | Cyclododecene | " | p-Toluenesufonic Acid | " | Phosphomolybdic Acid | " | " | " | 3.0 | 45.6 | 84.2 |
| 24 | Phonylcyclohexene | " | p-Toluene sulfonic Acid | " | Phosphomolybdic Acid | " | " | " | " | 37.3 | 75.3 |
| 25 | Cyclopentene | " | p-Toluenesulfonic Acid | " | Phosphomolybdic Acid | " | " | 100 | " | 78.5 | 97.6 |
| 26 | Cyclooctene | " | p-Toluenesulfonic Acid | " | Phosphomolybdic Acid | " | " | " | " | 45.4 | 88.6 |

What is claimed is:

1. A process for the preparation of a cyclic alcohol from a cyclic olefin which comprises subjecting a cyclic olefin represented by the formula:

$$C_nH_{2n-2-m}R_m$$

wherein
R represents a hydrogen atom, an alkyl group having 1 to 4 carbon atoms, a phenyl group or a cyclohexyl group,
n is an integer of from 5 to 12, and
m is an integer of from 1 to 4, to catalytic hydration reaction using a reaction system including the cyclic olefin and an aqueous solution comprising water and an aromatic sulfonic acid as a catalyst and wherein said aqueous solution further comprises at least one heteropoly acid which contains, as poly atom, at least one member selected from the group consisting of Mo, W and V and further contains, as central atom, at least one member selected from the group consisting of P, As, Si, Ge, Ti, Ce, Th, Mn, Ni, Te, I, Co, Cr, Fe, Ga, B, V, Pt, Be and Zn, and in which the poly atom and the central atom are present in an atomic ratio of from 2.5 to 12, and said catalytic hydration reaction is carried out at a temperature within the range of from 50° to 200° C.

2. A process according to claim 1, wherein the aromatic sulfonic acid is at least one member selected from the group consisting of benzenesulfonic acid, naphthalenesulfonic acid, anthracenesulfonic acid and ($C_1$–$C_3$) alkyl mono- or di-substituted derivatives thereof.

3. A process according to claim 1, wherein the aromatic sulfonic acid is alkylbenzenesulfonic acid.

4. A process according to claim 3, wherein the alkylbenzenesulfonic acid is p-toluenesulfonic acid.

5. A process according to claim 1, wherein the heteropoly acid is at least one member selected from the group consisting of a phosphomolybdic acid, a phosphotungstic acid, a phosphomolybdotungstic acid, a phosphomolybdovanadic acid, a phosphomolybdotungstovanadic acid, a phosphotungstovanadic acid, a phosphomolybdoniobic acid, a phosphomanganesetungstic acid, a silicomolybdic acid, a silicotungstic acid, a silicomolybdotungstic acid, a silicomolybdotungstovanadic acid, a boromolybdic acid, a borotungstic acid, a boromolybdotungstic acid, a boromolybdovanadic acid, a boromolybdotungstovanadic acid, a cobaltmolybdic acid and a cobalttungstic acid.

6. A process according to claim 5, wherein the heteropoly acid is at least one member selected from the group consisting of a phosphomolybdic acid, a phosphotungstic acid, a silicotungstic acid and a borotungstic acid.

7. A process according to claim 1, wherein the cyclic olefin is cyclohexene.

8. A process according to claim 1, wherein the cyclic olefin contains at least one member selected from the group consisting of an aromatic hydrocarbon and a cyclic paraffin.

9. A process according to claim 1, wherein the water is employed in an amount of 0.5 to 1000 in terms of molar ratio of the water to the cyclic olefin.

10. A process according to claim 1, wherein the total amount of the aromatic sulfonic acid and heteropoly acid is 5 to 80% by weight based on the amount of the aqueous solution.

11. A process according to claim 1, wherein the heteropoly acid is employed in an amount of 0.001 to 70% by weight based on the amount of the aqueous solution.

12. A process according to claim 1, wherein said catalytic hydration reaction is carried out under a pressure sufficient to keep the cyclic olefin and water in a liquid state at the reaction temperature.

13. In a catalytic hydration reaction system suitable for producing a cyclic alcohol from a cyclic olefin, the combination of an aromatic sulfonic acid and at least one heteropoly acid in an aqueous medium, each heteropoly acid containing, as poly atom, at least one member selected from the group consisting of Mo, W and V and further containing, as central atom, at least one member selected from the group consisting of P, As, Si, Ge, Ti, Ce, Th, Mn, Ni, Te, I, Co, Cr, Fe, Ga, B, V, Pt, Be and Zn, and in which the poly atom and the central atom are present in an atomic ratio of from 2.5 to 12.

14. A reaction system according to claim 13 comprising a catalytic amount of the aromatic sulfonic acid and an amount of the heteropoly acid sufficient to suppress corrosive action of said aromatic sulfonic acid.

15. A method of improving conversion of a cyclic olefin to a cyclic alcohol and concurrently suppressing corrosive action of an aromatic sulfonic acid catalyst in a catalytic hydration reaction system which comprises effecting the conversion in a reaction system according to claim 14.

16. In a process for preparing a cyclic alcohol from a cyclic olefin in a reaction system comprising an aromatic sulfonic acid as catalyst, the improvement wherein the reaction system comprises an aqueous medium having sufficient heteropoly acid to suppress corrosion otherwise attributable to the aromatic sulfonic acid.

* * * * *